United States Patent [19]

Miller et al.

[11] Patent Number: 4,501,602
[45] Date of Patent: Feb. 26, 1985

[54] PROCESS FOR MAKING SINTERED GLASSES AND CERAMICS

[75] Inventors: Stephen B. Miller, Corning; Ronald L. Stewart, Big Flats; David A. Thompson, Horseheads, all of N.Y.

[73] Assignee: Corning Glass Works, Corning, N.Y.

[21] Appl. No.: 418,215

[22] Filed: Sep. 15, 1982

[51] Int. Cl.³ ............................................. C03B 19/06
[52] U.S. Cl. ............................. 65/18.2; 65/18.3; 427/255
[58] Field of Search .............. 65/18.2, 18.3, 60.52, 65/18.1; 427/255, 167, 166

[56] References Cited

U.S. PATENT DOCUMENTS

| | | | |
|---|---|---|---|
| 2,694,651 | 11/1954 | Pawlyk | 117/106 |
| 2,734,874 | 2/1956 | Drake et al. | 252/461 |
| 3,049,797 | 8/1962 | Drummond | 29/194 |
| 3,081,200 | 3/1963 | Tompkins | 117/213 |
| 3,202,054 | 8/1965 | Mochel | 88/106 |
| 3,356,527 | 12/1967 | Moshier et al. | 117/107.2 |
| 3,801,294 | 4/1974 | Schultz et al. | 65/18 |
| 3,850,665 | 11/1974 | Plumat et al. | 65/60.52 |
| 3,883,336 | 5/1975 | Randall | 65/18 |
| 3,894,164 | 7/1975 | Dismukes | 427/157 X |
| 3,944,684 | 3/1976 | Kane | 427/255 X |
| 4,141,710 | 2/1979 | Aulich et al. | 65/3 A |
| 4,173,459 | 11/1979 | Aulich et al. | 65/3 A |
| 4,250,210 | 2/1981 | Crosby | 427/255 X |
| 4,378,987 | 4/1983 | Miller | 65/18.2 X |

FOREIGN PATENT DOCUMENTS

| | | |
|---|---|---|
| 57-51146 | 3/1982 | Japan . |
| 1454378 | 3/1976 | United Kingdom . |
| 2017669 | 10/1979 | United Kingdom . |
| 2033374 | 5/1980 | United Kingdom . |
| 2071644 | 9/1981 | United Kingdom . |

OTHER PUBLICATIONS

R. E. Sievers et al., "Volatile Metal Complexes", *Science* 201, (4352), 217–223, (Jul. 1978).
S. C. Chattoraj et al., "Hexafluoroacetylacetonates of Zirconium and Hafnium", *Proc. 1967 Int. Symp. Decomp. Organometallic Cmpds. to Refractory Ceramics*, pp. 77–98, (U. Dayton Press, 1978).
R. L. Van Hemert et al., "Vapor Depn. by Hydrogen Reduction of Metal Chelates", *J. Electrochem Soc.* 112, (11), 1123–1126, (Nov. 1965).
J. J. Gebhart, "Thermal Decomposition of Beryllium Acetylacetonate Between 1600°–2000° C.", *Proc. 1967 Int. Symp. Decomp. Organometallic Cmpds. to Refractory Ceramics*, pp. 319–329, (U. Dayton Press, 1978).
*Vapor Deposition*, C. F. Powell et al., Editors, pp. 389–391, 403, Wiley-New York, (1966).
R. L. Hough, "Chemical Vapor Deposition of Metal Oxides from Organometallics", *Proc. Third Int. Conf. on Chemical Vapor Deposition*, 232–241, American Nuclear Society, (1972).

*Primary Examiner*—Kenneth M. Schor
*Attorney, Agent, or Firm*—K. van der Sterre

[57] ABSTRACT

Glass or ceramic products including glass optical waveguides are produced by a vapor phase oxidation process wherein β-diketonate complexes of selected metals having significant vapor pressures at some temperature below their decomposition temperatures are vaporized, transported to an oxidation site in the vapor phase, and reacted in the vapor phase to form particulate metal oxide soot. After capture, this soot can be consolidated by sintering to form e.g. clear glass of a purity suitable for drawing into glass optical waveguide fiber.

5 Claims, 4 Drawing Figures

PROCESS FOR MAKING SINTERED GLASSES AND CERAMICS

BACKGROUND OF THE INVENTION

The present invention is in the field of ceramic processing and relates particularly to a method for making pure glass or ceramic products by vapor deposition and subsequent sintering.

The favored commercial practice in the manufacture of very pure glass products such as glass optical waveguides is by vapor deposition. The process conventionally involves the transport of vaporized reactants to an oxidation site, e.g., a burner or hot plasma zone adjacent to a deposition substrate or within a glass deposition tube, oxidation of the reactants at the oxidation site to form a particulate oxide or soot oxidation product on the mandrel or tube, and finally processing of the deposited soot to convert it to clear glass.

The vaporization characteristics of the reactants are critical for such processing. In commercial practice, these reactants have consisted of the volatile halides or hydrides of the selected metals or metalloids, e.g., the halides or oxyhalides of silicon, phosphorus, germanium and boron. These compounds have high vapor pressures at temperatures which are easy to maintain in a vapor delivery system and are converted to pure oxides at the oxidation site. In some cases, systems which operate at temperatures above the boiling temperature of the volatile halide or oxyhalide compound at atmospheric pressure have been used.

Suggestions have been made that other volatile compounds of these metals, such as the organometallic compounds, could be used, but there has been no commercial application of this proposal in the waveguide field. GB No. 2,071,644 suggests that silanes, chloro- and alkyl-substituted silanes, and/or silicate esters can be used in vapor delivery systems for optical waveguide production, but in general the instability, high reactivity, and/or limited vapor pressures of such compounds have mitigated against their use.

It has been recognized that it would be desirable to use many of the common glass modifying oxides such as MgO, $Na_2O$, $Al_2O_3$, CaO and the like in the fabrication of glass optical waveguides by vapor deposition techniques, but no satisfactory technique for incorporating these oxides in vapor deposited glass has yet been developed. Most of the main group and rare earth metals useful as modifiers in transparent glasses do not form volatile chlorides or other volatile but stable inorganic compounds. Thus, although they have potential utility as modifying dopants in glass waveguides, no successful technique for incorporating these oxides in vapor-deposited glass in high purity and with close control over concentration has been developed.

Proposals have been made to use metal alkyls as metal sources for the vapor deposition of oxides but these compounds are generally so unstable as to be hazardous. For example, the compounds trimethylaluminum, $Al(CH_3)_3$ and dimethylzinc, $Zn(CH_3)_2$ are volatile and reactive, but are pyrophoric and thus very dangerous to store and to use.

U.S. Pat. No. 3,801,294 discloses an early approach to the incorporation of main group modifiers in vapor deposited oxide glasses wherein direct vaporization of metal halides from the solid state is proposed. This approach is disadvantageous because high delivery system temperatures must be maintained to achieve even moderate vapor pressures, and it is difficult to control the concentrations of dopants present in the carrier gas stream.

U.S. Pat. No. 3,883,336 proposes an alternative approach for incorporating main group oxides in vapor deposited glass wherein a solution containing a soluble salt of the desired metal is nebulized and the dispersed solution directed into an oxidation flame wherein metal oxide soot is generated. Unlike solvent-free vapor phase oxidation, this approach does not reproducibly provide an oxide soot with a particle size distribution such that it can be sintered into a void-free homogeneous mixed-oxide glass or ceramic. Moreover, the solvents used are potential sources of contamination in the product. Neither particulate oxide inclusions nor contaminating impurities can be tolerated in optical waveguide glass.

U.S. Pat. Nos. 4,141,710 and 4,173,459 suggest an alternative technique for using solutions wherein a solvent carrying a thermally decomposable organic or inorganic compound of the desired metal is supplied to the inner surface of a bait tube or crucible. This process is one of thermal decomposition, rather than vapor phase oxidation, and is therefore not well suited to the fabrication of glass optical waveguides. The deposits produced by hot-surface thermal decomposition again differ significantly in morphology from the soots produced by vapor phase oxidation, and often exhibit cracking and flaking if thick. Consequently, such deposits can be very difficult to convert to defect-free glass. Thus, while the thermal decomposition of inorganic and organometallic compounds, including metal chelates such as the acetylacetonates, has been used to produce thin oxide films on glass sheet (G.B. No. 1,454,378 and G.B. No. 2,033,374A), and for metal plating (U.S. Pat. No. 3,356,527 and U.S. Pat. No. 3,049,797), such practices are not commercially adaptable to the fabrication of bulk glass products such as optical waveguides.

It is therefore a principal object of the present invention to provide a method for making glass or other pure ceramic products which permits the incorporation of main group and rare earth metal oxides into such products without undesirable voids or compositional discontinuities such as particulate oxide inclusions.

It is a further object of the invention to provide a method for fabricating glass optical waveguides incorporating such metal oxides as dopants wherein good control over the concentration of dopants in the vapor-deposited glass and high purity in the vapor deposition product can be achieved.

Other objects and advantages of the invention will become apparent from the following description thereof.

SUMMARY OF THE INVENTION

The present invention involves the use of selected vaporizable chelates of selected main group and rare earth metals as vapor sources for the manufacture of pure glass and ceramic products by the consolidation of oxide soot produced by vapor phase oxidation. The process follows that presently used for the deposition of pure oxide glass formers and glass modifiers for products such as optical waveguides, in that the metal compounds are vaporized and transported as vapor to an oxidation site where the compounds are reacted in the vapor phase to form finely divided soot. In current practice, this oxide soot is then captured and consolidated by heating to produce clear glass which can ultimately be formed into a product such as an optical waveguide fiber. Such vapor deposition processes are advantageous because they permit the fabrication of very pure glass or ceramic products, i.e., products made of amorphous or crystalline materials incorporating not more than about 0.01% by weight total of metallic impurities.

Metals which can be transported in accordance with the invention may be selected from Groups IA, IB, IIA, IIB, IIIA, IIIB, IVA, IVB and the rare earth series of elements of the Periodic Table. These are provided as preparations of stable metal chelate compounds which can be vaporized at moderate temperatures and transported at substantial partial pressures. The transported chelate vapors are converted by vapor phase reaction at the reaction site to finely divided oxide soot having particle sizes and a particle size distribution suitable for capture and consolidation into a unitary or monolithic product, preferably a clear glass. The metal chelates used in the process are selected metal $\beta$-diketonates, i.e., complexes of the metal with one or more $\beta$-diketonate ligands derived from the class of diketones known as $\beta$-diketones. The $\beta$-diketonate complex may include diketonate ligands only, or additional ligands may be present in the complex as adducts to the metal chelate structure.

Compounds selected from this group are liquids or solids at ambient temperatures and pressures. They are relatively stable against oxidation in air, yet can exhibit vapor pressures of over 10 mm Hg and frequently over 100 mm Hg at temperatures below their decomposition temperatures. The selected compounds exhibit sufficient stability to be transported at these temperatures without significant decomposition, yet are readily reacted in the vapor phase to form pure metal oxides in the presence of oxygen at the reaction site, with or without additional heating depending upon the particular vapor phase reaction induced.

Utilizing these compounds, main group and rare earth elements may be transported in vapor form to a reaction site in substantial but controllable concentrations without the use of a solvent carrier, so that high purity oxides of these metals in very finely-divided form suitable for sintering to clear glasses or fine-grained ceramics may be provided.

BRIEF DESCRIPTION OF THE DRAWINGS

The invention may be further understood by reference to the drawings, wherein.

DETAILED DESCRIPTION

Figure 2:
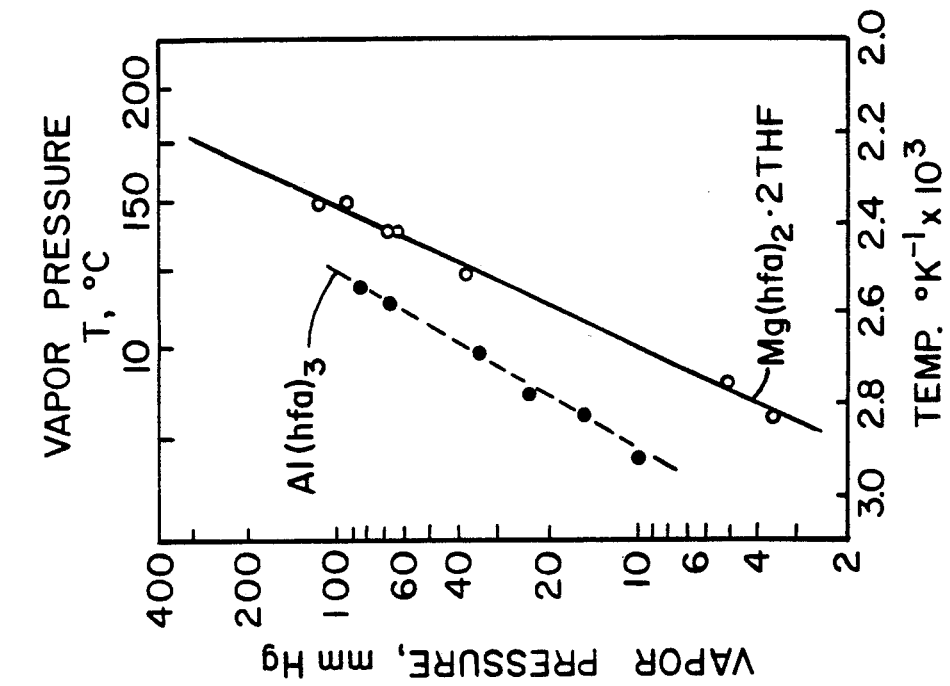
FIG. 2 consists of vapor pressure data for selected $\beta$-diketonate compounds suitable for use in accordance with the invention.

Oxides to be deposited by vapor phase oxidation in accordance with the invention include the oxides of metals selected from Groups IA, IB, IIA, IIB, IIIA, IIIB, IVA and IVB of the Periodic Table. These may include oxides capable of forming glasses, e.g. aluminum oxide, but are predominantly oxides used as intermediates or modifiers in glass-forming systems, eg. the alkali and alkaline earth metal oxides. Examples of candidate metals selected from these groups are as follows: Group IA—Li and Na; Group IB—Cu; Group IIA—Be, Mg; Group IIB—Zn, Cd, Hg; Group IIIB—Sc, Y; Group IIIA—Al, Ga; Group IVA—Sn, and Group IVB—Zr and Hf.

Rare earth metal oxides may also be deposited by vapor phase oxidation in accordance with the invention. An example of a rare earth metal oxide which can be advantageously used as a dopant in optical waveguide glass is $CeO_2$, which in trace amounts can improve the resistance of waveguides to radiation damage. Other rare earth oxides which have been considered for use as glass modifiers in fused silica waveguides are La and Yb.

To be suitable for use in a vapor delivery system for vapor phase reaction, compounds of metals selected for incorporation in the deposited oxide must have a significant vapor pressure at some temperature below the compound's decomposition temperature. This vapor pressure requirement varies depending upon both the concentration of metal oxide needed in the deposition product and the deposition rate desired, but can range from as little as 1 mm Hg for a compound needed in only trace amounts to a vapor pressure of at least about 10 mm Hg and preferably at least 100 mm Hg for compounds to be incorporated as major intermediate or glass-modifying constituents of the deposited glass.

The structure of the metal $\beta$-diketonate molecule is known to consist of a metal atom surrounded by $\beta$-diketone ligands of the general formula: $[R—CO—CH—CO—R']^-$. The R and R' constituents are typically alkyl or fluorinated alkyl groups containing 1–4 carbon atoms. It is known that, for any given metal, the volatility of the corresponding metal $\beta$-diketonate depends strongly on the identity of the R and R' constituents.

Unsubstituted, low-molecular-weight diketones such as acetylacetone (2,4-pentanedione) have been used to form soluble metal complexes for the formation of metal oxide films by thermal decomposition against heated substrates. However, metal $\beta$-diketonates incorporating these ligands do not generally exhibit sufficient vapor pressures below their decomposition temperatures to be useful vapor sources for the formation of main group metal oxides by vapor phase oxidation according to the invention.

In contrast, metal $\beta$-diketonates wherein the $\beta$-diketone ligands are of higher formula weight (i.e., at least about 153) and particularly wherein they are derived from fluorinated diketones, can exhibit significantly higher vapor pressures, and thus can be used to generate significant volumes of metal-containing vapors for the vapor phase generation of oxide soot. It has been theorized that the enhanced volatility of fluorine-substituted $\beta$-diketonate complexes is due to an effect on the van der Waals forces among chelate molecules caused by the high electronegativity of fluorine (R. E. Sievers et al., *Science*, 201 [4352] pp 217–223). For large fluorine-free ligands, steric hindrance may be a factor.

Examples of fluorinated and/or high molecular weight $\beta$-diketones suitable for complexing with main group or rare earth metals to form volatile metal chelates are reported in Table I below. Included in Table I for each named compound are a molecular structure for each compound, a symbol or trivial name used as a shorthand notation for the compounds in subsequent Examples, and boiling temperatures for each compound (reported at 760 mm Hg except where otherwise indicated). The H prefix in each of the shorthand notations (e.g., Hhfa) refers to the neutral compound in diketone form, whereas the diketonate anion form is written without the prefix (hfa)⁻.

TABLE I
Structures and Properties of β-diketones Used as Ligands

| Compound | Structure | Trivial Name (Symbol) | Boiling Point |
|---|---|---|---|
| 1,1,1 trifluoro-2,4-pentanedione | $F_3C-\overset{O}{\underset{\|}{C}}-CH_2-\overset{O}{\underset{\|}{C}}-CH_3$ | trifluoroacetylacetone (Htfa) | B.P. = 107° C. |
| 1,1,1,5,5,5 hexafluoro-2,4-pentanedione | $F_3C-\overset{O}{\underset{\|}{C}}-CH_2-\overset{O}{\underset{\|}{C}}-CF_3$ | hexafluoroacetylacetone (Hhfa) | B.P. = 70° C. |
| 2,2,6,6-tetramethyl-3,5-heptanedione | $(H_3C)_3C-\overset{O}{\underset{\|}{C}}-CH_2-\overset{O}{\underset{\|}{C}}-C(CH_3)_3$ | (Hthd) or (Hdpm) | B.P. = 214–216° |
| 6,6,7,7,8,8,8-heptafluoro-2,2-dimethyl-3,5-octanedione | $(H_3C)_3C-\overset{O}{\underset{\|}{C}}-CH_2-\overset{O}{\underset{\|}{C}}-(CF_2)_2-CF_3$ | (Hfod) | B.P. = 33° |
| 2,2,7-trimethyl-3,5-octanedione | $(H_3C)_3C-\overset{O}{\underset{\|}{C}}-CH_2-\overset{O}{\underset{\|}{C}}-CH_2-CH(CH_3)_2$ | (Htod) | B.P. = 55° C. (0.1 mm Hg) |
| 1,1,1,5,5,6,6,7,7,7-decafluoro-2,4 heptanedione | $F_3C-\overset{O}{\underset{\|}{C}}-CH_2-\overset{O}{\underset{\|}{C}}-CF_2-CF_2-CF_3$ | (Hdfhd) | B.P. = 99–105° C. |
| 1,1,1-trifluoro-6-methyl-2,4 heptanedione | $F_3C-\overset{O}{\underset{\|}{C}}-CH_2-\overset{O}{\underset{\|}{C}}-CH_2-CH(CH_3)_2$ | (Htfmhd) | |

Because of the practical requirement of high volatility, the use of the fluorinated β-diketonates of the main group and rare earth metals constitutes the preferred procedure for the vapor phase reaction of main group metals in accordance with the invention, and the use of one or more of the fluorinated ligands from Table I above is particularly preferred.

The mechanism of bonding in β-diketonate complexes is almost always through the oxygen atoms of the ligand, after deprotonation of the diketone to give the anion, as follows:

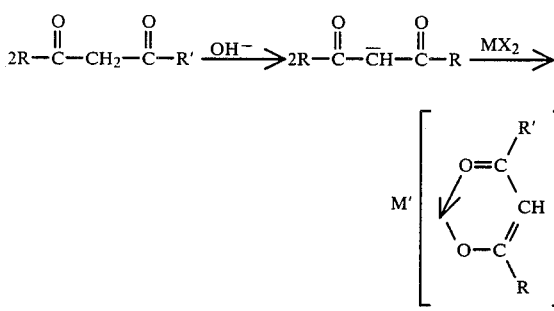

As is well known, the charge on the diketonate anion is actually delocalized about the —CO—CH—CO— functional group, rather than at the central carbon atom as shown.

β-diketonate complexes usually exhibit high solubility in non-polar organic solvents, e.g., hexane, carbon tetrachloride or the like, with much lower solubility in alcohols or water. Methods for preparing these complexes have been described in the literature. See, for example, *Metal β-Diketonates and Allied Derivatives*, R. C. Mehrotra, R. Bohra and B. P. Gaur, Academic Press, New York (1978).

Examples of specific β-diketonate complexes of metals which should exhibit vapor pressures of at least about 10 mm Hg without significant decomposition at temperatures of 250° C. or below, and thus should be suitable sources of those metals for reaction by vapor phase oxidation to provide metal oxides, are indicated in Table II below. Table II includes a listing of the metals as elements together with an indication of which ligands are suitable for complexing therewith, the latter being identified by their commonly used symbols as reported in Table I above.

TABLE II
Volatile β-Diketonate Complexes

| Elements | (tfa)⁻ | (hfa)⁻ | (thd)⁻ | (dfhd)⁻ | (fod)⁻ |
|---|---|---|---|---|---|
| Li | | | X | | |
| Na | | | X | | |
| Be | X | X | | | |
| Mg | | X | | X | |
| Sc | X | | X | | |
| Y | | | X | | X |
| Cu | X | X | | | X |
| Hf | | | | | X |
| Ti | | X | | | |
| Zr | | X | | | |
| Zn | X | X | X | | |
| Cd | | X | | | |
| Al | X | X | | | X |
| Ga | X | X | | | |
| Ce | | | | | X |

Where only minor concentrations of a selected oxide are to be incorporated in a soot product, vapor pressures as high as 10 mm Hg may not be required and pressures as low as 1 mm Hg may provide sufficient metal vapor concentrations. An example of such a case is the incorporation of cerium oxide as a trace dopant to suppress radiation discoloration in a silicate core glass for an optical waveguide, where concentrations exceeding about 0.1% $CeO_2$ by weight are rarely needed. $Ce(tod)_4$ is an example of a rare earth metal β-diketonate which, while not demonstrating vapor pressure as high as some of the fluorinated β-diketonates hereinabove described exhibits sufficient vapor pressure to constitute a suitable vapor source for generating a small concentration of cerium oxide by vapor phase oxidation. Of course, even for trace doping a more convenient practice would be to use a higher vapor pressure complex, such as $Ce(fod)_4$, where such is available.

In many cases, β-diketonate complexes tend to form adducts with solvent molecules used in preparation, particularly when the complex is not coordinatively saturated and the solvent is a good Lewis base. The resulting adducted β-diketonate complexes can be quite stable and can themselves exhibit sufficient stability and volatility to constitute useful vapor sources. Examples of compounds which form adducts with β-diketonates are ammonia, water, pyridine, bipyridyl, phenanthroline, tetrahydrofuran and dimethylformamide. These attach to the complex as additional ligands to achieve six-fold or higher coordination with the metal.

The method by which metal oxide soot is captured and consolidated to form a glass or other product, after being generated by the vapor phase oxidation of β-diketonate complexes in accordance with the invention, is not critical. Essentially any prior art soot processing technique can be used, including but not being limited to capturing the soot a suitable mandrel or bait rod, capturing the soot in a collection container, consolidating the captured soot by sintering on or off the bait or after shaping the loose soot by compaction or slip-casting, and treating the captured soot prior to or during consolidation to remove non-metallic impurities such as water, carbon or fluorine therefrom.

The following examples describe β-diketonate compounds which have been prepared and, based on their properties, are presently considered suitable for use as main group metal sources for the production of pure oxides suitable for glass formation by vapor phase oxidation processes.

EXAMPLE 1—Al(hfa)$_3$

A β-diketonate complex of aluminum (a Group IIIA metal) is prepared by reacting hexafluoroacetylacetone (Hhfa) with aluminum chloride. A 1.06 g sample of $AlCl_3$ is added to 10 ml of $CCl_4$ with stirring under nitrogen. A solution of (Hhfa) in $CCl_4$ is slowly added to the $AlCl_3$ solution, with large amounts of HCl being evolved during the addition. The reaction mixture is refluxed for 30 minutes and the hot mixture is thereafter passed through a frit filter.

The clear filtrate crystallizes on cooling to give about 5.21 g of a white crystalline product. This product is purified by vacuum sublimation at 80° C. into a dry ice-cooled cold trap.

Infrared spectral analysis of a sample of the product in KBr corresponds to that reported in the literature for Al(hfa)$_3$. This compound sublimes readily at temperatures above 50° C., melts at about 72°–74° C., and has a reported vapor pressure of about 100 mm Hg at 125° C. This indicates that the compound would be a suitable source of aluminum-containing vapors for the production of sinterable oxide soot by a vapor phase reaction process.

EXAMPLE 2—Mg(hfa)$_2$

β-diketonate complexes of the Group IIA metal magnesium are prepared by reacting (Hhfa) with basic magnesium carbonate. A 2.5 g sample of basic magnesium carbonate, 4 $MgCO_3.Mg(OH)_2$. $nH_2O$ (n≈6), is suspended in 100 ml of ether with stirring under nitrogen. A 10.41 g sample of (Hhfa) is added to the suspension and the mixture is refluxed for two hours. The ether is then separated from a solid residual phase by decantation and evaporated to dryness. Evaporation leaves a residual white powder product identified as the ether-water adduct of magnesium hexafluoroacetylacetonate, Mg(hfa)$_2$.1.5Et$_2$O.H$_2$O. This adducted complex melts at about 225° C. and can be vaporized by sublimation at 165° C.

To prepare a tetrahydrofuran (THF) adduct of Mg(hfa)$_2$, a 20 ml volume of THF is added to the ether-water adduct produced as described above and the resulting solution is stirred for 18 hours. Rotary evaporation of the solution leaves a white powder residue identified by proton nuclear magnetic resonance (nmr) as Mg(hfa)$_2$.4THF. Sublimation of this compound to a dry ice-cooled cold trap produces the adduct Mg(hfa)$_2$.2THF, a compound having a melting point of approximately 130° C. which can be vaporized at 160° C. to generate Mg-containing vapors for a vapor phase oxidation process.

EXAMPLE 3—Na(tfmhd)

A β-diketonate complex of the Group IA metal sodium is prepared by reacting sodium hydroxide with a beta-diketone containing a 7-carbon chain. A 4.08 g sample of pelletized NaOH is dissolved in 50 ml of water in a separatory funnel and 20.0 g of the diketone 1,1,1-trifluoro-6-methyl-2,4-heptanedione (Htfmhd) is added to the solution. This mixture is shaken periodically over a 15-minute interval, and then ether is added to extract the Na β-diketonate product from the mixture. The pale yellow ether extract is evaporated to dryness in air giving a pale yellow solid identified as Na(tfmhd), having an undetermined melting point but giving evidence of sublimation at about 260° C. with some evidence of thermal decomposition.

EXAMPLE 4—Ce(fod)$_4$

A β-diketonate complex of the rare earth metal cerium is prepared by reacting cerium nitrate with 6,6,7,7,8,8,8-heptafluoro-2,2-dimethyl-3,5-octanedione.

A 68.2 g sample of this β-diketone (Hfod) is added to 115 ml of 2 M aqueous $NH_4OH$, resulting in a white precipitate which is separated and dissolved in 200 ml of water and 200 ml of methanol. The resulting solution is placed in an addition funnel and added dropwise to a nitric acid solution of cerium nitrate consisting of 25.0 g Ce(NO$_3$)$_3$.6H$_2$O dissolved in 60 ml of 1.4 M HNO$_3$. 2 M NH$_4$OH is then added to achieve and maintain a pH of 6.

The resulting mixture separates into a red oil phase and an aqueous phase. The separated mixture is stirred under $O_2$ at room temperature until oxidation of $Ce^{+3}$ to $Ce^{+4}$ is complete, in this case about 70 hours. Thereafter, 200 ml of hexanes are added and the organic layer containing the product is separated from the aqueous phase, filtered, and evaporated to dryness in a rotary evaporator. The product is crystallized from the red oil, and examination of the proton nmr spectrum of the crystals shows substantially complete oxidation to Ce(fod)$_4$.

After purification by sublimation, the Ce(fod)$_4$ thus produced exhibits a melting point of about 97° C. and a vapor pressure approaching 10 mm Hg at a temperature near 200° C. By virtue of this high vapor pressure this compound would constitute a suitable source of Ce-containing vapors for a vapor phase oxidation process in accordance with the present invention.

EXAMPLE 5—Zn(hfa)$_2$.1.5 THF

Following the procedure reported by Chattoraj et al. in *J. Inorg. Nucl. Chem.*, 28 (1966), pages 1937–1943, the water adduct of Zn(hfa)$_2$ is prepared by reacting Hhfa with zinc oxide. Ten grams of ZnO and 35.2 ml of Hhfa are added to a flask equipped with a condenser, magnetic stirrer and heating mantel, with stirring to disperse the ZnO. Thirty ml of H$_2$O is added, causing the reflux of Hhfa due to the evolution of heat, with stirring being continued until all evidence of reaction has ceased.

An additional 30 ml of water and 200 ml of ether are then added and the mixture is refluxed for one hour. After cooling, excess ZnO is removed by filtration, the ether layer is separated and dried by adding 4Å molecular sieves, crude Zn(hfa)$_2$.2H$_2$O product.

Approximately 10 g of this product is dissolved in THF at room temperature, the solvent is then evaporated, and the residue is sublimed at 150° C. under vacuum to a dry ice-cooled cold trap. Infrared spectra, nuclear magnetic resonance, thermogravimetric analysis, elemental analysis, and differential scanning calorimetry are used to characterize this compound. The compound is presently believed to have the chemical formula Zn(hfa)$_2$.2THF, with a melting temperature of 165° C. It exhibits excellent thermal stability, showing only slight decomposition when held at 165° C. for about 60 hours.

Neither the methods of preparing Zn(hfa)$_2$.2THF, Mg(hfa)$_2$.nTHF, and Ce(fod)$_4$ disclosed in Examples 2, 4 and 5 above nor the compounds themselves comprise any part of the present invention, these being described and claimed in two copending, commonly assigned patent applications of David A. Thompson, Ser. Nos. 418,061 and 418,216, concurrently filed herewith.

Figure 1:
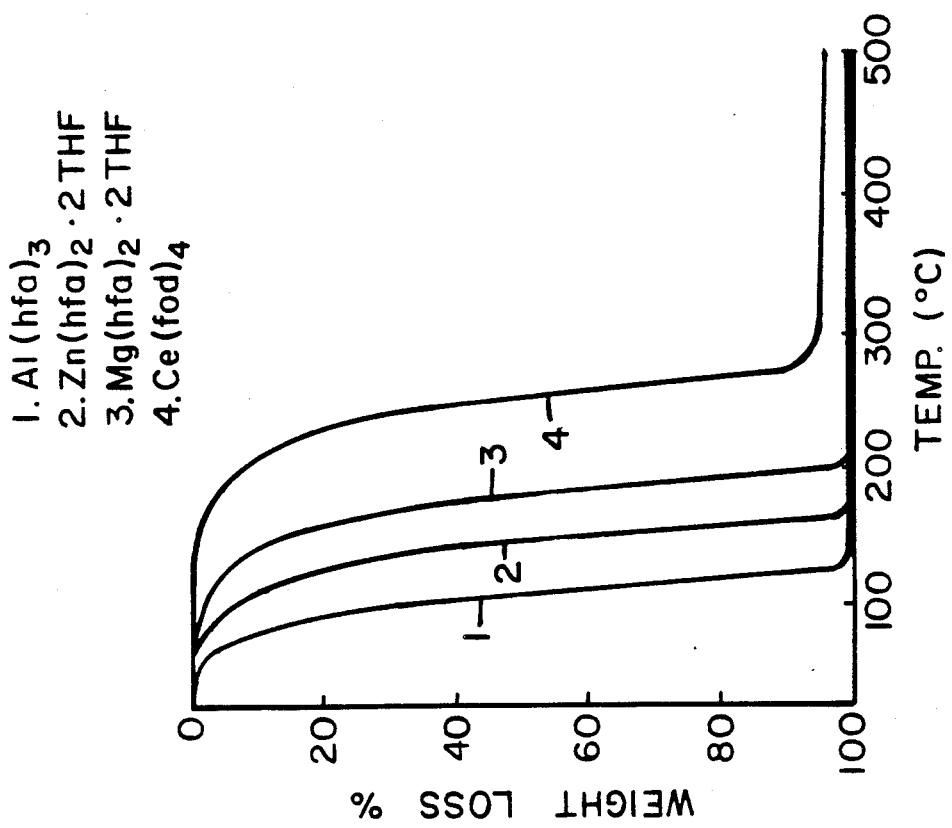
FIG. 1 consists of thermogravimetric curves for selected $\beta$-diketonate compounds suitable for use in accordance with the invention.

FIG. 1 of the drawings demonstrates the vaporization characteristics of selected β-diketonate complexes such as reported in the above examples, as determined by thermogravimetric analysis. The drawing plots weight loss of a sample of the complex as a function of temperature over the heating range from about 25°–500° C. Temperature is plotted on the horizontal axis with the vertical axis corresponding to relative weight loss in the sample.

In general, easy vaporization without decomposition is reflected by an analysis trace exhibiting a sharp vertical drop corresponding to rapid weight loss of the heated sample in the evaporation or sublimation range, followed by a sharp horizontal trace at higher temperatures evidencing the absence of decomposable residues. The most desirable vaporization characteristics are demonstrated by Al(hfa)$_3$, Zn(hfa)$_2$.2THF and Mg(hfa)$_2$.2THF, which exhibit rapid and complete vaporization at temperatures in the 100°-200° C. range. This may be contrasted with the behavior of a complex such as Mg(hfa)$_2$.PCl$_3$, an adducted complex hereinafter described with reference to FIG. 3, which exhibits evidence of significant decomposition and incomplete volatilization even at temperatures in excess of 300° C.

FIG. 2 of the drawings plots vapor pressure as a function of temperature for the Al(hfa)$_3$ and Mg(hfa)$_2$.2THF β-diketonate complexes. This drawing shows the very substantial vapor pressures of these two complexes, which are in the range of at least 10–100 mm Hg at temperatures in the range of 100°–200° C.

Significant variations in volatility can occur when β-diketonate compounds such as above described are complexed with Lewis bases to form adducted metal β-diketonates. To demonstrate some of these variations, adducts of Mg(hfa)$_2$ with five different Lewis bases are prepared by adding small quantities of the sublimed ether-water adduct Mf(hfa)$_2$.1.5Et$_2$O.H$_2$O to diethyl ether solutions of each of the six adducts: pyridine, CH$_3$CN, PCl$_3$, dioxane and dimethyl formamide (DMF), with overnight stirring followed by evaporation to dryness and sublimation under vacuum to obtain the products. The volatility of each of the adducts is then evaluated by thermogravimetric analysis.

Figure 3:
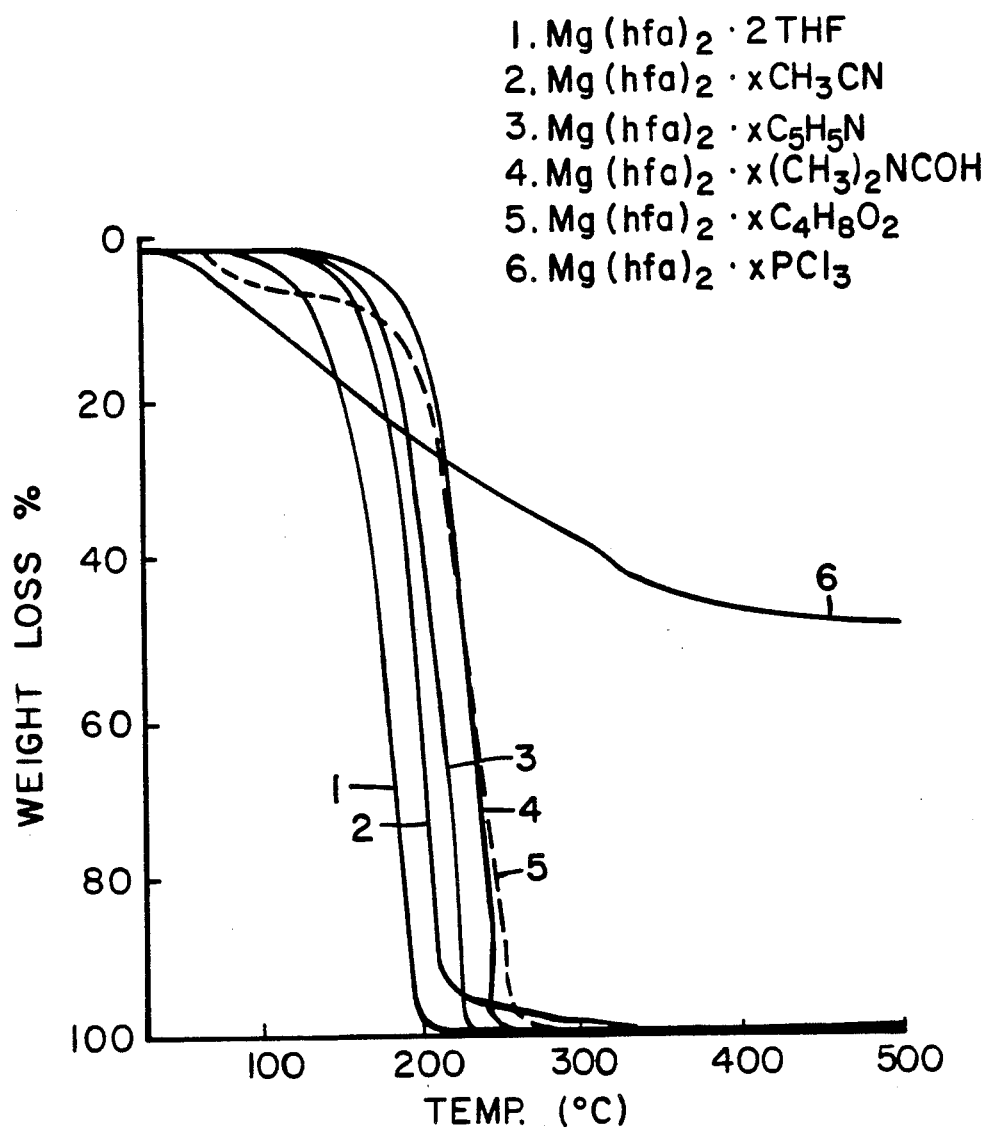
FIG. 3 consists of thermogravimetric curves showing the effects of adduct variation on the volatility of some adducted $\beta$-diketonate compounds.

FIG. 3 of the drawings sets forth thermogravimetric curves for the five different adducts Mg(hfa)$_2$.xL where L is pyridine (C$_5$H$_5$N), CH$_3$CN, PCl$_3$, dioxane (C$_4$H$_8$O$_2$) or DMF ((CH$_3$)$_2$NCOH) as indicated in the drawing. The proportions x of these L ligands in the adduct molecules were not determined. A curve for Mg(hfa)$_2$.2THF is also included for comparison. The CH$_3$CN and PCl$_3$ adducts show evidence of decomposition, while the other adducts evaporate completely within narrow ranges of temperature, but at vaporization temperatures which vary significantly depending upon the identity of the particular adduct employed. Mg(hfa)$_2$.2THF is found to be the most volatile of the various adducts tested.

The requirement that the metal compound be sufficiently volatile for efficient vaporization and vapor phase transport in accordance with the invention arises because of the need to generate a soot product with a relatively small particle size. For example, to obtain void-free glasses by the viscous sintering of oxide soot, particle sizes not exceeding about 0.1 microns are normally preferred. The following examples demonstrate the utility of selected volatile β-diketonate compounds for the production by vapor phase oxidation of fine, homogeneous oxide soot.

EXAMPLE 6—γAl$_2$O$_3$

A quantity of Al(hfa)$_3$ produced as in Example 1 above is maintained in a liquid state in a glass container by heating to about 125° C. A helium carrier gas is bubbled through the liquid Al(hfa)$_3$ (the latter having a vapor pressure of about 100 mm Hg at this temperature) and the He carrier then transports vaporized Al(hfa)$_3$ out of the container to an operating flame-oxidation burner through a heated delivery line. The flame oxidation burner is of the kind described in U.S. Pat. No. 4,125,288, having a design permitting the introduction of a vapor reactant stream into the burner flame via a center orifice in the burner face.

Figure 4:
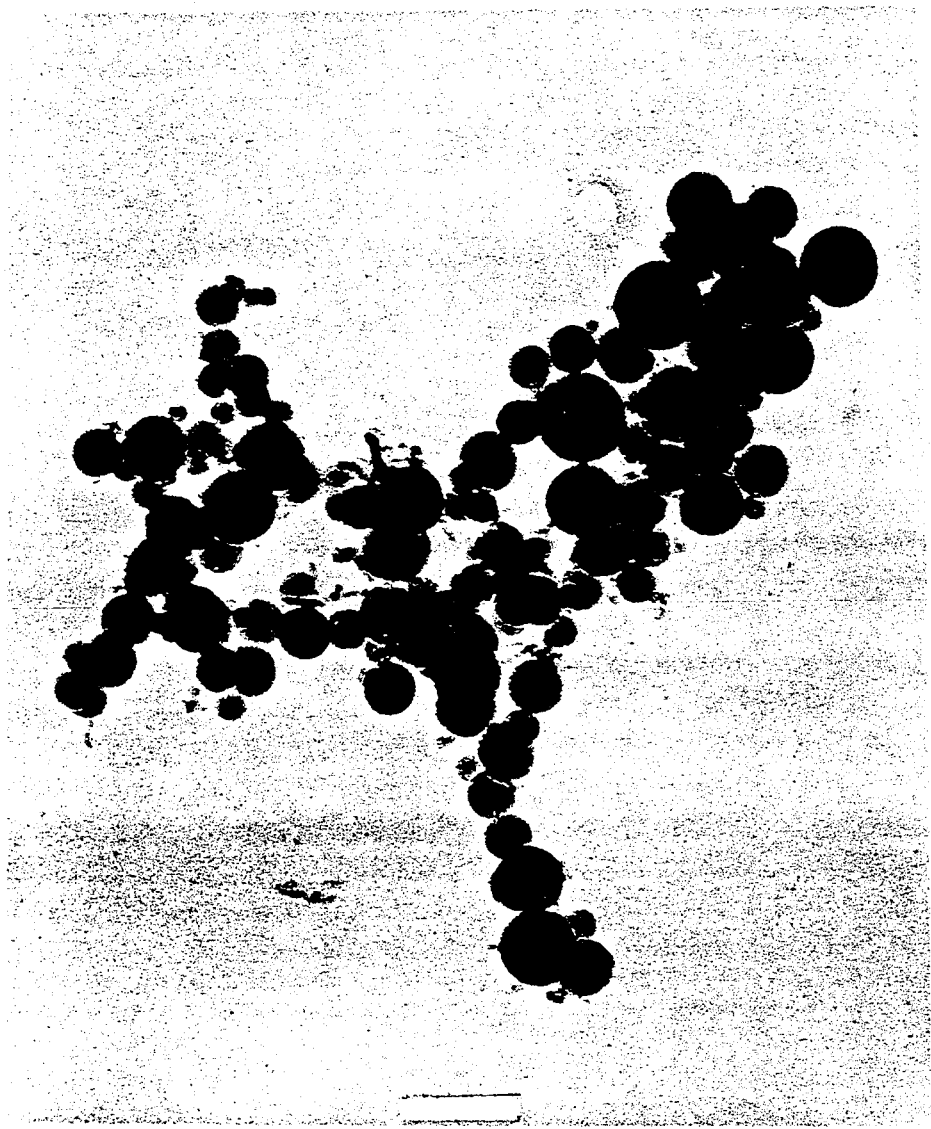
FIG. 4 is an electron photomicrograph of a captured metal oxide soot provided in accordance with the invention.

The Al(hfa)$_3$ is oxidized in the vapor phase in the methane-oxygen burner flame to produce a γ-Al$_2$O$_3$ soot which is collected for examination. FIG. 4 of the drawing is an electron photomicrograph of a sample of the γ-Al$_2$O$_3$ soot thus provided, wherein the bar corresponds to a dimension of 0.1 microns.

As is evident from a study of FIG. 4, the γ-Al$_2$O$_3$ soot produced by Al(hfa)$_3$ oxidation in accordance with the invention is in the form of very small (<0.1 microns)

spherical particles, the bulk of which range from about 0.025-0.05 microns in size. This indicates that the material could readily be incorporated into ceramics or void-free glasses of a desired composition by a sintering consolidation process.

EXAMPLE 7—MgO-SiO$_2$ Glass

A quantity of Mg(hfa)$_2$.2THF produced as described in Example 3 above is maintained in a liquid state in a glass container by heating to about 190° C., a temperature at which it has a vapor pressure of about 500 mm Hg. An argon carrier gas is bubbled through this liquid at a rate of about 72 cc/min., and vaporized Mg(hfa)$_2$.2THF is transported by this carrier through a heated delivery line to an operating methane-oxygen burner of the type used in Example 6 above.

A second reactant stream, transported by a second delivery line and combined with the Mg(hfa)$_2$.2THF-carrying stream at the burner, is produced by bubbling argon at a rate of 576 cc/min through a quantity of SiCl$_4$ maintained at 35° C., a temperature at which SiCl$_4$ has a vapor pressure of 530 mm Hgl. The combined reactant stream is fed into the burner flame, that flame resulting from the combustion of 3.5 l/min. of natural gas (methane) and 3.4 l/min. of oxygen.

The SiCl$_4$ and Mg(hfa)$_2$.2THF reactants are converted by vapor phase oxidation in the flame to SiO$_2$ and MgO, each in the form of a finely divided oxide soot. This soot mixture is collected on an alumina mandrel for examination, analysis and further treatment.

Analysis of the collected soot determines that a soot mixture consisting of 1.21% MgO and the remainder SiO$_2$ has been deposited on the mandrel. This soot mixture is consolidated by heating with a gas-oxygen flame to sinter the soot into a clear MgO-SiO$_2$ glass having a refractive index of about 1.460.

EXAMPLE 8—MgO-SiO$_2$ Opal Glass

The glass-forming procedure of Example 8 is repeated, except that argon carrier gas flow through the liquid Mg(hfa)$_2$.2THF reactant is increased to 720 cc/min., such that the soot mixture collected from the vapor phase oxidation of the reactant stream contains 7.74% MgO and the remainder SiO$_2$ by weight. This soot mixture is sintered in a gas-oxygen flame as in Example 6, and the product is a dense, substantially void free MgO-SiO$_2$ opal glass.

In using β-diketonate complexes as sources of main group metals for vapor phase oxidation processes, it must be recognized that these complexes can undergo reactions at vapor delivery temperatures which can adversely affect the desirable vaporization and stability characteristics thereof. Reactions to be considered which might reduce the volatility of the complex include electrophilic substitution of a halogen for a hydrogen atom on the β-diketone ligand, adduct formation by the complexing of the β-diketonate molecule with selected bases, replacement reactions wherein a β-diketonate ligand is replaced by a halide and redistribution reactions wherein ligands are scrambled among various metal complexes to produce new complexes of low volatility. Avoidance of these reactions may require the use of delivery systems wherein each vaporized reactant is separately transported to the reaction site for final mixing and vapor phase oxidation.

While the foregoing description has been primarily concerned with processes suitable for the formation of optically clear glasses useful, for example, in the fabrication of glass optical waveguides, it will be appreciated that the method of the invention could also be employed in the manufacture of other pure unitary ceramic products such as opal glasses, semicrystalline glasses, or crystalline ceramics, including porous glasses or ceramics where only partial sintering of the oxide soot is permitted in the consolidation step. In addition, it is possible to process the oxide soot prior to consolidation if, for example, it is desired to shape the soot into a preform of a desired configuration. This can be done, for example, by dispersing the soot in a suitable vehicle and casting the dispersion into a selected shape. Thus the foregoing examples are merely illustrative of procedures and products which may be provided in accordance with the invention as set forth in the appended claims.

We claim:

1. In a method for making a glass or ceramic article by a vapor phase oxidation process wherein vaporized glass or ceramic source compounds are oxidized while in the vapor phase to form particulate oxide soot, the oxide soot is captured as deposited soot in a collection container or on a deposition substrate, and the deposited soot is sintered by heating to form a void-free, monolithic self-supporting glass or ceramic article, the article having a composition which includes at least one modifying oxide of a metal selected from Groups IA, IB, IIA, IIB, IIIA, IIIB, IVA, IVB and the rare earth series of the Periodic Table, the improvement wherein:
    (a) the vaporized source compound for at least one of the constituent metal oxides of the article is a β-diketonate complex of the selected metal;
    (b) the β-diketonate complex of the selected metal exhibits a vapor pressure of at least 10 mm (Hg) at a temperature below 250° C.;
    (c) the β-diketonate complex can be vaporized at a temperature below 250° C. without significant thermal decomposition, as evidenced by thermogravimetric analysis; and
    (d) the vaporized β-diketonate complex can be and is oxidized in the vapor phase to produce oxide particles of the selected metal wherein the oxide particles do not exceed about 0.1 microns in diameter.

2. A process in accordance with claim 1 wherein the selected metal is selected from the group consisting of Li, Na, Be, Mg, Sc, Y, Zr, Hf, Ti, Zn, Cd, Al, Ga, Tl and Ce, and wherein the β-diketonate complex includes β-diketonate ligands which have a formula weight of at least 153 and incorporate fluorinated alkyl groups.

3. A method in accordance with claim 2 wherein the β-diketonate ligands are selected from the group consisting of (tfa), (hfa), (thd), (dfhd), (tod) and (fod) ligands.

4. A method in accordance with claim 3 wherein the β-diketonate complex is adducted with at least one Lewis base.

5. A method in accordance with claim 4 wherein the Lewis base is tetrahydrofuran.

* * * * *

UNITED STATES PATENT AND TRADEMARK OFFICE
CERTIFICATE OF CORRECTION

PATENT NO. : 4,501,602

DATED : February 26, 1985

INVENTOR(S) : S. B. Miller, R. L. Stewart & D. A. Thompson

It is certified that error appears in the above-identified patent and that said Letters Patent is hereby corrected as shown below:

Col. 5, lines 55 and 59 in the equation, "$+2^{x^-}$" and "$_2$" were omitted.

Col. 9, line 25, after "sieves," insert -- filtered, and the ether is then evaporated to give 55 g of --.

Signed and Sealed this

Seventeenth Day of February, 1987

Attest:

DONALD J. QUIGG

Attesting Officer     Commissioner of Patents and Trademarks